United States Patent [19]
Parins et al.

[11] Patent Number: 5,743,906
[45] Date of Patent: Apr. 28, 1998

[54] ENDOSCOPIC BIPOLAR BIOPSY FORCEPS

[75] Inventors: David J. Parins, Corcoran; Richard Keith Poppe, Minneapolis, both of Minn.

[73] Assignee: Everest Medical Corporation, Minneapolis, Minn.

[21] Appl. No.: 713,168

[22] Filed: Sep. 12, 1996

Related U.S. Application Data

[62] Division of Ser. No. 375,953, Jan. 20, 1995, Pat. No. 5,603,711.

[51] Int. Cl.$^6$ .......................... A61B 17/39; A61B 10/00
[52] U.S. Cl. .......................... 606/51; 128/751
[58] Field of Search .......................... 606/45, 46, 48–52; 128/751

[56] References Cited

U.S. PATENT DOCUMENTS

| | | | |
|---|---|---|---|
| 4,953,559 | 9/1990 | Salerno | 606/39 |
| 5,217,458 | 6/1993 | Parins | 128/751 |
| 5,295,990 | 3/1994 | Levin | 128/751 |
| 5,352,222 | 10/1994 | Rydell | 606/37 |
| 5,482,054 | 1/1996 | Slater et al. | 128/751 |

FOREIGN PATENT DOCUMENTS

| | | | |
|---|---|---|---|
| 0593929 | 4/1994 | European Pat. Off. | 606/52 |
| 2355521 | 1/1978 | France | 606/52 |

*Primary Examiner*—Lee S. Cohen
*Attorney, Agent, or Firm*—Haugen & Nikolai, P.A.

[57] ABSTRACT

A bipolar biopsy device comprising two biopsy tissue collecting receptacles wherein at least one biopsy tissue collecting receptacle is pivotable in relation to the other and wherein each biopsy tissue collecting receptacle supports an electrode portion thereon to which current can flow and a cutting edge that is electrically insulated from the electrode portion. The electrode portion coagulates the tissue surrounding the cutting portion. The cut tissue sample is retained within the receptacles so that it maybe removed for biopsy purposes. Preferably, each biopsy receptacle is individually pivotable in relation to the other and the device is dimensioned to have utility in endoscopic or similar procedures.

20 Claims, 2 Drawing Sheets

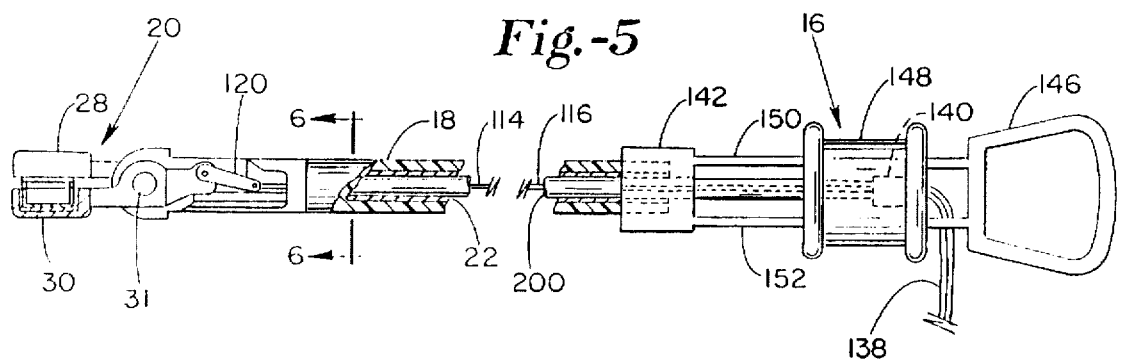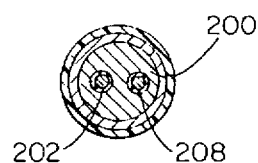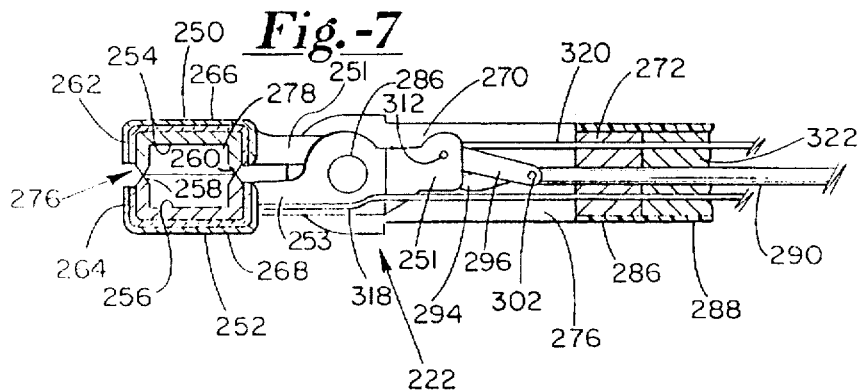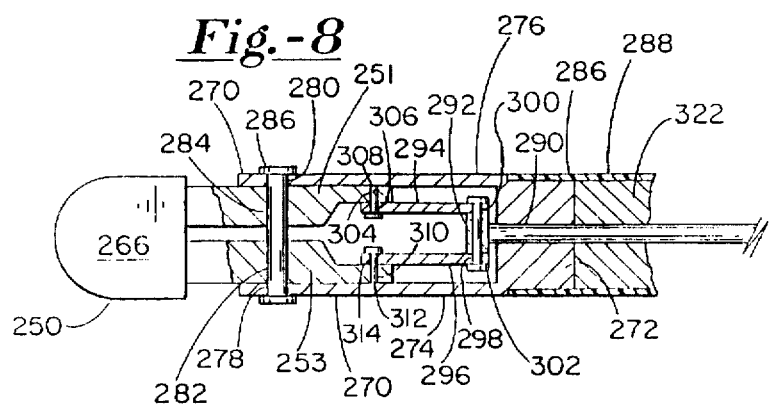

5,743,906

ENDOSCOPIC BIPOLAR BIOPSY FORCEPS

This is a Divisional of application Ser. No. 08/375,953, filed on Jan. 20, 1995, now U.S. Pat. No. 5,603,711.

I. FIELD OF THE INVENTION

This invention relates generally to a bipolar biopsy instrument, and more particularly to a bipolar biopsy instrument incorporating tissue specimen collecting receptacles with coagulation and mechanical cutting features, such that electrocoagulation and mechanical Cutting of the tissue specimen retained within the biopsy receptacles can be achieved without requiring an instrument exchange.

II. BACKGROUND OF THE INVENTION

Obtaining tissue samples for diagnostic purposes is a commonly performed surgical procedure known as a biopsy. Such a procedure requires two steps: cutting a tissue specimen and then retrieving the cut tissue specimen. Electrosurgical devices are well-known surgical instruments which have been used in biopsy procedures for coagulation the tissue removal site. Coagulation of the tissue occurs with electrocoagulating instruments including at least one conductive electrode. Radio frequency (RF) energy is conducted through this electrode to either a remote conductive body plate (monopolar) or to a second, closely spaced conductive electrode (bipolar). Current passing through the space between the two electrodes will coagulate the blood and other body fluids placed between them.

In bipolar electrosurgical instruments, the two electrodes are closely spaced to one another, usually at the distal end of an instrument handle. The return path is very short and only involves the tissue and fluids in a short path between the two electrodes. Electrosurgical devices can also cut tissue by applying a voltage across two electrodes causing an arc discharge which creates such a high heat energy that the cells comprising the tissue are desicated.

A bipolar electrosurgical biopsy instrument where the two tissue specimen collecting members mechanically cut the tissue specimen and are also electrically insulated from one another and comprise the bipolar electrodes for electrocoagulation are known. Metal-to-metal contact along sharpened edges of cutting electrode surfaces of a bipolar instrument can result in an electrical short. Furthermore, the attempt to use a rivet or a screw as the pivot point for the biopsy tissue specimen collecting receptacles is another area where short-circuiting is likely to occur. When such a short exists, the electrical current does not flow through the body or tissue to effect coagulation, but instead, follows the short circuit path from one electrode to another. Additionally, the histological integrity of the tissue specimen is not always maintained when electrodes are used for both cutting of the tissue specimen and coagulation of the removal site.

Certain bipolar instruments have been developed incorporating metal cutting surfaces which also act as electrodes. For example, bipolar scissors have been developed with blades at the distal tip performing coagulation and cutting of the tissue with a mechanical shearing action. The two blades are effectively insulated from one another, allowing them to function as bipolar electrodes for electrocoagulating small blood vessels in the surgical field. U.S. Pat. No. 5,352,222 discloses such a surgical scissors with bipolar coagulation features. While surgical scissors are utilized in a coagulation and cutting operation, a need exists for a single instrument to be used in biopsy procedures which require coagulation, cutting and intact removal of the tissue specimen. In the past, biopsy procedures often have required an exchange of instruments to perform these steps.

A need, therefore, exists for a single bipolar electrosurgical biopsy device where the coagulating electrodes are in close proximity to the mechanical cutting surfaces (since they are both located on the tissue specimen collecting receptacles) and yet, isolates the tissue specimen from the electrodes to maintain histological integrity.

SUMMARY OF THE INVENTION

It is accordingly a principle object of the present invention to provide a bipolar electrosurgical biopsy instrument having a metal cutting edge located on the specimen collecting members of the biopsy device for the mechanical cutting of the tissue specimen with the outer surface of the specimen collecting members also acting as electrodes for coagulating the tissue.

Another object of the present invention is to provide a bipolar electrosurgical biopsy device having metal (stainless steel) biopsy specimen collecting members with metal cutting edges that are electrically insulated from the coagulating electrodes also contained on the metal biopsy specimen collecting members in close proximity to the metal cutting edge.

Yet another object of the present invention is to present a bipolar electrosurgical biopsy device that maintains histological integrity of the collected specimen after the application of coagulating energy.

Still another object of the present invention is to provide a bipolar biopsy device with coagulating and cutting features contained on the tissue specimen collecting members so as to avoid the need to switch between instruments during a biopsy procedure, thus making the biopsy procedure more efficient and easier to perform.

A further object of the present invention is to provide a bipolar biopsy device having a miniaturized distal tissue specimen collecting member that allows the instrument to be inserted through a cannula, a laparoscope or the working lumen of an endoscope.

The foregoing objects of the present invention are achieved by providing an instrument having two opposing stainless steel tissue specimen collecting biopsy members. In a first embodiment, the tissue specimen collecting biopsy members each comprise a cup-like receptacle with at least one of the cups being metal having a sharpened perimeter surface thereon. The cup-like receptacles are affixed by a non-conductive adhesive to the interior of a metal support, which is made to act as an electrode. That is to say, an electrically insulating bonding layer is disposed intermediate the tissue specimen collecting receptacle and a support therefor which functions as an electrode when energized.

In a second embodiment, at least one of the tissue specimen collecting receptacles is a conductive material such as stainless steel. An insulating layer coats the exterior of the stainless steel receptacle and then a conductive layer is coated on top of the insulating layer. The conductive layer is wired to a RF voltage source and acts as an electrode.

The biopsy instrument of both embodiments has the tissue collecting receptacles pivotally secured to the distal end of an elongated tube. An actuating link extends through the tube to a moveable portion of a handle so that when the handle is manipulated, the biopsy receptacles can be made to open and close relative to one another. Also, extending through the lumen from electrical terminals on the handle to the electrodes are conductors which permit a voltage to be applied between the two electrodes.

When the biopsy receptacles are closed around the tissue specimen to be coagulated, cut and retrieved, the metal cutting surfaces come in contact with each other after cutting through the tissue whereas a gap remains between the electrode supports or the electrode coatings to allow coagulation of the tissue therebetween when the electrode surfaces are energized. As the biopsy receptacles have a sharpened cutting edge and the sharpened cutting edge is insulated from the receptacles' electrode supports or the conductive coatings, there will be no short circuit between the electrode and the metal cutting surfaces as the device closes around the tissue to be cut and retained within the biopsy receptacle.

DESCRIPTION OF THE DRAWINGS

The foregoing features, objects, and advantages of the invention will be come apparent to those skilled in the art from the following detailed description of a preferred embodiment, especially when considered in conjunction with the accompanying drawings in which like numerals and the several views refer to corresponding parts.

FIG. 5 is a side elevational and partially cross-sectioned view of the bipolar biopsy device in accordance with an alternative handle construction;

FIG. 6 is a cross-sectional view taken along line 6—6 in FIG. 5;

FIG. 7 is an enlarged side elevational view of the distal portion of the bipolar biopsy device in accordance with an alternative biopsy tissue collecting member construction, the drawing being partially sectioned to illustrate the working elements of the alternative embodiment; and FIG. 8 is a top view of the alternative embodiment with the figure being partially cross-sectioned.

DETAILED DESCRIPTION OF A PREFERRED EMBODIMENT

Figure 1:
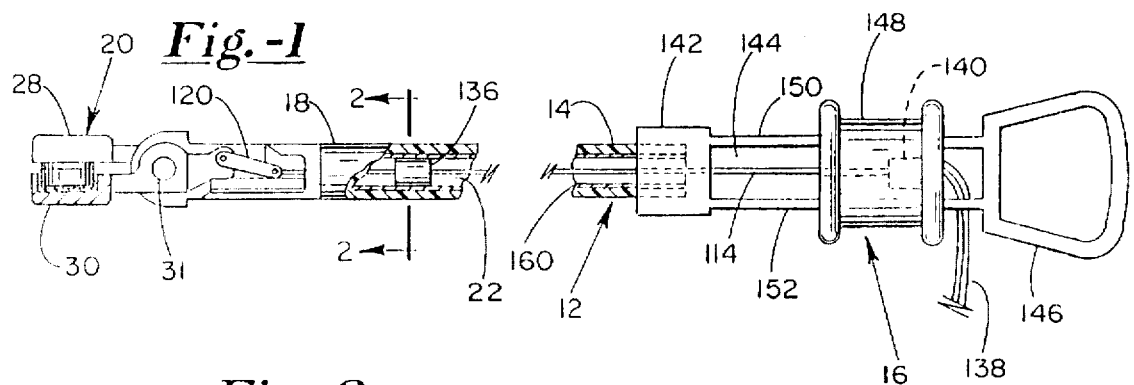
FIG. 1 is a side elevation view of a biopsy device having two moveable biopsy tissue collecting members, the drawing being partially sectioned to illustrate the working elements of the embodiment.

Referring to FIG. 1, the bipolar biopsy device is shown for use in endoscopic or other similar scope-type procedures. The biopsy device has an elongated tubular member 12 of a diameter and length sufficient for use in cooperation with a procedure performed using a scope type instrument. The tubular member 12 has a proximal end 14 affixed to a handle assembly 16, a distal end 18 containing the biopsy tissue collecting assembly 20, and a lumen 22 which extends for the entire length of tubular member 12. As shown in the cross-sectional view of FIG. 2, the tubular member 12 comprises a metal tube 24, such as stainless steel, coated over its exterior with an electrical insulator 26. The electrical insulator 26 is preferably a polymer such as TEFLON®. In addition to being an insulator, such a coating provides a lubricous surface which enhances its slidability through the lumen of an endoscope.

Press fit into the distal end 18 of the tubular member 12 is the biopsy tissue collecting assembly 20. The biopsy tissue collecting assembly 20 comprises a first jaw member 28 and a second jaw member 30 pivotally joined to each other by an insulated rivet or screw 31 which extends through aligned bores formed through the two jaw members 28 and 30. Both jaw members 28 and 30 are, thus, pivotally moveable with respect to each other.

Figure 2:
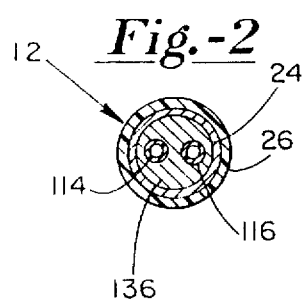
FIG. 2 is a cross-section view along line 2—2 of FIG. 1.
Figure 3:
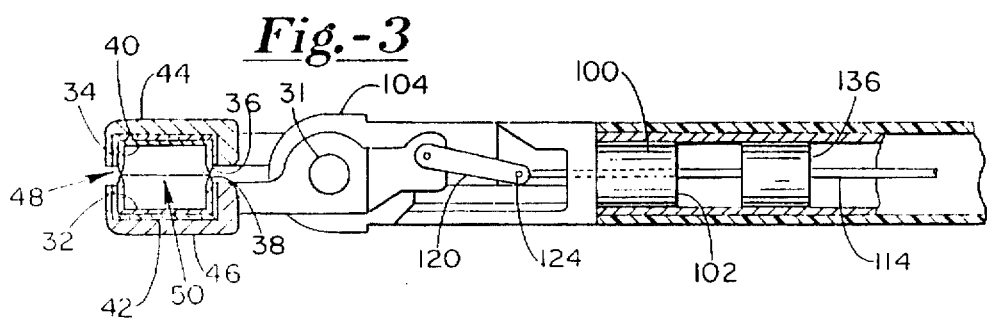
FIG. 3 is an enlarged side elevation view of the distal portion of FIG. 1 with the drawing being partially sectioned.
Figure 4:
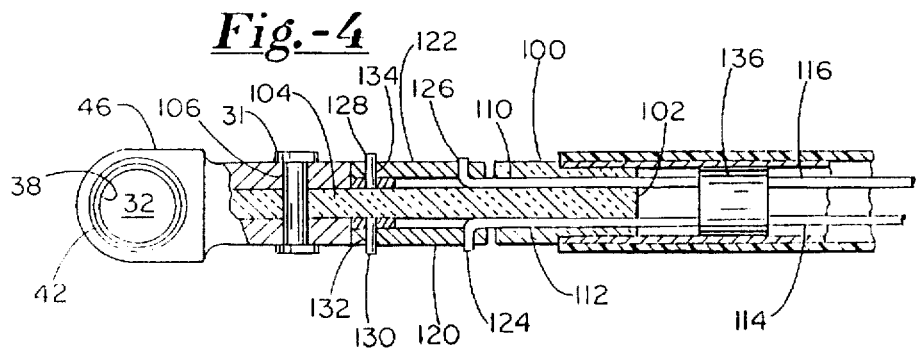
FIG. 4 is a top view of the distal end with the drawing being partially sectioned.

Each biopsy jaw member 28 and 30 has an electrically conductive support 44 and 46 as shown in FIG. 2. Tissue specimen collecting cup like receptacles 32 and 34 are formed in the facing surfaces of the electrically conductive supports 44 and 46. The receptacles 32 and 34 are designed to contain cup shaped members therein. As shown in FIGS. 3 and 4, each receptacle 32 and 34 has a peripheral edge 36 and 38 sharpened for cutting the tissue specimen. Insulating layers 40 and 42 are disposed between the specimen collecting receptacles 32 and 34 and the electrically conductive supports 44 and 46 and act to bond each receptacle to its respective support. The insulating layers 40 and 42 can be made of any suitable insulating material and are preferably a non-conductive adhesive such as an epoxy adhesive. The electrically conductive supports 44 and 46 act as electrodes and are made of metal, preferably stainless steel. At least one of the receptacles 32 and 34 is made of metal, preferably stainless steel. The other may likewise be made of metal or other suitable material such as plastic. If it is not made of metal, it does not need a sharpened cutting edge, but may provide a surface for the opposing cutting edge to contact.

As can be seen in FIGS. 1 and 3, the cutting edges 36 and 38 extend beyond the outer surface of the electrode supports 44 and 46. Thus, when the biopsy assembly is in the closed position, the sharpened cutting edges 36 and 38 contact each other, whereas an isolating space 48 exists between the two electrodes supports 44 and 46. Thus, when RF current is applied to the electrode supports the tissue which surrounds the area contained within the receptacles 32 and 34 is cauterized. The cutting edges 36 and 38 mechanically cut the tissue specimen and then the specimen is retained with the cavity 50 formed when the biopsy assembly 20 is in the closed position.

As is evident in FIGS. 3 and 4, the biopsy tissue collecting assembly 20 comprises, in addition to the biopsy members 28 and 30, an insulated base 100 having a proximal portion 102 and a distal portion 104. The distal portion 104 has a bore 106 therethrough which provides a frame to which the electrode supports 44 and 46 of jaw members 28 and 30 are pivotally attached, via the pivot pin or screw 31. The proximal portion 102 of the base 100 is preferably press fit within the tubular member 12 and has two parallel longitudinal bores 110 and 112 through which two rigidly electrically conductive rods 114 and 116, each preferably covered with a layer of electrical insulation, pass. With reference to FIGS. 1 and 2, it is seen that the two rods 114 and 116 extend through the lumen 22 of the tubular member 12.

Referring to FIGS. 1, 3 and 4, which show the distal portion of the instrument 10, the rods 114 and 116 are pivotally coupled to their respective biopsy jaw members 28 and 30 by respective rigid links 120 and 122. The distal ends of the rods 114 and 116 are turned laterally outwardly to fit through respective proximal pivot point openings 124 and 126 of the links 120 and 122 to thereafter form a rivet type connection. Situated at each of the proximal portions of the jaw members 28 and 30 are lateral projecting posts 128 and 130 which pass through distal pivot openings 132 and 134 of the links 120 and 122 and likewise form rivet type connections. The rigid links 120 and 122 thereby can pivot at each of their respective proximal and distal end portions.

Proximal to the base 100 within the tubular member 12 is disposed an insulator member 136 through which rods 114 and 116 pass. The insulator member 136 functions to electrically isolate the rods 114 and 116 from each other while mechanically acting to maintain them in a parallel, spaced-apart condition as they traverse the lumen 22. As seen in FIG. 1, the respective proximal end portions of the rods 114 and 116 extend out from the proximal end of the tubular member 12 and terminate in a electrical connector 140 contained on the handle assembly. External leads originating from an electrosurgical generator (not shown) as known in the art provides current to the connector 140 to thereby provide current to the rods 114 and 116, links 120 and 122 and electrode supports 44 and 46.

Disposed at the proximal end 14 of the tubular member 12 is the handle assembly 16 of the type commonly used in gastrointestinal endoscopic procedures. The handle assembly 16 has a stationary member 142 with a longitudinal slot 144 extending therein. A ring member 146, intended to receive a thumb of the operator, is located at the proximal end of the stationary member 142. The distal end of the stationary member contains two bores for receiving the rods 114 and 116 therethrough. A reciprocating spool member 148 forms the moveable member of the handle assembly 16. Spool 148 has two bores for receiving walls 150 and 152 defining the longitudinal slot 144 therethrough. The spool 148 is thus configured to reciprocate along these walls 150 and 152. The spool 148 additionally has bores for receiving the proximal ends of rods 114 and 116. The rods 114 and 116 extend through apertures in the distal end of the stationary member 142 into the longitundinal slit 144 and are secured to the spool 148. The rods 114 and 116 terminate in the electrical connector 140, also located in spool 148, which receives the external leads 138 from the electrosurgical generator.

As evident from FIG. 1, operation of the handle assembly 16 by sliding the spool 148 towards the distal end of the handle assembly translationally moves both of the rods 114 and 116, causing the biopsy jaw members 28 and 30 to close. Likewise, moving the spool 148 towards the proximal end of the handle assembly causing the biopsy jaw members 28 and 30 to open. Biopsy jaw members 28 and 30 are thereby pivotally opened and closed. In this manner, dual biopsy member movement is accomplished. If only a single jaw biopsy member movement is desired, it is understood that in such a known linkage arrangement only one biopsy member is joined to and pivotable by moving the moveable handle member of the handle assembly.

Referring to FIGS. 5 and 6, a slightly modified version of the handle embodiment of FIG. 1 is shown. The ceramic insulator-spacer 136 of FIG. 1 is replaced by an elongated double lumen tube 200, which is preferably formed from nylon or another lubricous polymer and which extends through the lumen 22 of the tubular member 12 substantially the entire length thereof. The double lumen extends through a bore formed in the proximal end of the stationary handle member and into the spool member to the electrical Connector. FIG. 7 shows a cross-sectional view taken through the barrel in the double lumen tube 200. The push rods 114 and 116 extend individually through the separate lumens 202 and 208 and thus remain electrically isolated from one another. In addition to providing this electrical isolation, the double lumen tube 200 also supports the push rods 114 and 116 along substantially their entire length to prevent any bowing thereof when the push rods are in compression upon actuation of the biopsy device. As such, the biopsy jaw members 28 and 30 are made to open and close in a more controlled fashion, thereby improving the "feel" of the device.

An alternative arrangement of the biopsy cup assembly 222 is shown in FIGS. 7 and 8. Biopsy jaw members 250 and 252 consist of two tissue specimen collecting cup shaped receptacles 254 and 256 with edges 258 and 260 honed for cutting. The tissue specimen collecting receptacles 254 and 256 are preferably made of a metal such as stainless steel. The exterior of each receptacle 254 and 256 is coated with an insulating material such as ceramic, glass, a high temperature plastic, or another nonconductive material. These coatings 262 and 264 are preferably 1–5 mils thick. Conductive coatings 266 and 268 are deposited or otherwise placed over the insulative coatings 262 and 264, respectively. These conductive coatings 266 and 268 are preferably metal traces which are paste-printed or electro-plated onto the insulative nonconductive material of coatings 262 and 264. These metal traces can be composites, silver, gold, palladium, platinum, or other metal suitable for use on medical instruments. The conductive coating 266 and 268 are preferably 1–5 mils thick. As with the first embodiment, only one of the receptacles needs to have the sharpened cutting edge. The remaining cup shaped receptacle need not be made of metal and can be of any suitable material such as plastic.

The biopsy tissue collecting assembly 222 of the second embodiment comprises, in addition to the biopsy members, an insulated frame 270 having a proximal portion 272 and a distal portion consisting of two side members 274 and 276. Each side member has a bore, 278 and 280, aligned with bores 282 and 284 located on the proximal end of the biopsy tissue collecting recepticals 250 and 252. A pivot pin 286 for enabling the receptacles 250 and 252 to be pivotably moveable with respect to each other extends through bores 282 and 284 on the receptacles 250 and 252 and bores 278 and 280 on the side members 274 and 276 of the insulated frame 270. The side members 274 and 276 thus provide a support to which the biopsy tissue collecting receptacles 250 and 252 are attached. The proximal portion 272 of frame 270 has a tubular configuration and is press fit into the distal end 286 of the tubular member 288.

The mechanism used to open and close the biopsy receptacles 250 and 252 of this embodiment incorporates a single, nonconductive push rod 290 and corresponding linkage, although any actuation mechanism which results in dual or single pivotal movement of the tissue specimen collecting receptacle is acceptable. The single push rod 290 extends from the spool 148 through the tubular member 288. The distal end of the single push rod 290 has a bore 292. Two links 294 and 296 are situated on opposing sides of the distal end and each has a bore, 298 and 300 respectively, aligned with the rod bore 292. A pivot pin 302 extends through bores 292, 298 and 300, pivotally securing the links 294 and 296 to the push rod 290.

Biopsy tissue collecting receptacle 250 has a bore 304 on its proximal end 251 which is aligned with a bore 306 on link 294. A pivot pin 308 extends therethrough and pivotally secures the biopsy receptacle 250 to the link 294. Likewise, biopsy tissue collecting receptacle 252 has a bore 310 on its proximal 253 end which is aligned with a bore 314 on link 296. A pivot pin 312 extends through these two bores to pivotally secure the biopsy receptacle 252 to the link 296. When the spool 148 is moved towards the distal end, the push rod 290 also moves towards the distal end. This causes links 294 and 296 to open at their distal ends which opens the biopsy receptacles 250 and 252. When rod 290 is moved towards the proximal end, the links 294 and 296 close, which in turn closes the biopsy receptacles 250 and 252.

Two conductive wires also extend through the tubular member 222 from the electrical connector located on the handle assembly to the conductive coatings 266 and 268 located on the tissue collecting receptacles 250 and 252. A first conductive wire 318 extends through the tubular member 222 to the conductive coating 268. The conductive wire 318 has an insulative covering to keep the wire electrically isolated and preventing any short circuiting. Likewise, a second conductive wire 320 extends through the tubular member to conductive coating 266 and it also has an insulative covering to electrically isolate the wire and prevent any short circuiting. In this embodiment it is preferable to use a triple lumen tube 322 which extends through the tubular member 222. The rod 190 and conductive wires 318 and 320 can extend through their individual lumens electrically isolated from each other and further to support them along their length.

The conductive coatings 266 and 268 cover only a portion of the insulative coatings 262 and 264 in order to create an isolating space 276. Thus, when the biopsy members are in the closed position and the sharpened cutting edges 258 and 260 have cut the tissue specimen to be retained within cavity 278, the application of RF current to the two conductive coatings 266 and 268 results in the cauterization of the tissue, vessels and the like located within the gap 276 and bridging the electrodes.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and details and operating procedures, can be accomplished without departing from the scope of the invention itself.

What is claimed:

1. A bipolar biopsy device comprising:

(a) a bipolar biopsy jaw arrangement having a first and second jaw member, said first jaw member is pivotable in relation to the second jaw member, a first tissue specimen collecting receptacle on a distal end of said first jaw member and a second tissue specimen collecting receptacle on a distal end of said second jaw member and a cutting edge on said first tissue specimen collecting receptacle;

(b) first conductive coating on said first tissue specimen collecting receptacle and a second conductive coating on said second tissue specimen collecting receptacle;

(c) a spacing means for electrically isolating said conductive coatings from said first and second tissue specimen collecting receptacles; and (d) means to supply a voltage across said conductive coatings.

2. The bipolar biopsy device of claim 1 wherein each said conductive coating includes metal traces.

3. The bipolar biopsy device of claim 1 wherein each said conductive coating has a thickness in the range of 1–5 mils.

4. The bipolar biopsy device of claim 1 and further including a first insulative layer positioned between said first conductive coating and said first tissue specimen collecting receptacle and a second insulative layer positioned between said second conductive coating and said second tissue specimen collecting receptacle.

5. The bipolar biopsy device of claim 4 wherein said first insulative layer has a thickness in the range of 1–5 mils and said second insulative layer has a thickness in the range of 1–5 mils.

6. A bipolar biopsy device comprising:

(a) an elongated tubular member having a proximal end, a distal end and a lumen extending therebetween;

(b) first and second biopsy collecting receptacles formed from electrically conductive material disposed at said distal end of the tubular member and configured to hold a tissue sample therebetween, said first biopsy collecting receptacle is pivotable in relation to the second biopsy collecting receptacle between an open position and a closed position;

(c) a cutting edge on said first biopsy collecting receptacle for cutting said tissue sample;

(d) a first electrode formed by a conductive coating on said first biopsy collecting receptacle and a second electrode formed by a conductive coating on said second biopsy collecting receptacle;

(e) a first insulating layer interposed between said first biopsy collecting receptacle and said first electrode and a second insulating layer between said second biopsy collecting receptacle and said second electrode;

(f) spacing means on said first and second biopsy collecting receptacles for electrically isolating said first electrode from said second electrode;

(g) a handle disposed at the proximal end of the tubular member, said handle being mechanically coupled to said first biopsy collecting receptacle; and (h) means extending through said lumen for applying a voltage between said first and second electrodes.

7. The bipolar biopsy device of claim 6 wherein said first conductive coating includes metal traces and said second conductive coating includes metal traces.

8. The bipolar biopsy device of claim 6 wherein said first conductive coating has a thickness in the range of 1–5 mils and said second conductive coating has a thickness in the range of 1–5 mils.

9. The bipolar biopsy device of claim 6 wherein said first insulating layer is a first insulative coating on said first biopsy collecting receptacle and said second insulating layer is a second insulative coating on said second collecting receptacle.

10. The bipolar biopsy device of claim 9 wherein said first insulative coating has thickness in the range of 1–5 mils and said second insulative coating has thickness in the range of 1–5 mils.

11. A bipolar electrosurgical instrument for biopsy procedures comprising:

(a) first and second biopsy jaw members, each comprising a coated tissue collecting receptacle including a cutting edge, an intermediate electrically insulative coating on an exterior of said receptacle, and an electrically conductive coating on an exterior of said intermediate coating;

(b) means for pivotally joining said first and second biopsy jaw members together with their respective cutting edges facing one another;

(c) means coupled to at least one said first and second biopsy members for imparting a closing and opening like movement relative to the other of said first and second biopsy members;

(d) a spacing means for electrically isolating said first biopsy member from said second biopsy member; and (e) means for applying a voltage between the electrically conductive coatings.

12. The bipolar electrosurgical instrument for biopsy procedures of claim 11 wherein said electrically conductive coating includes metal traces.

13. The bipolar electrosurgical instrument for biopsy procedures of claim 11 wherein said electrically conductive coating has a thickness in the range of 1–5 mils.

14. The bipolar electrosurgical instrument for biopsy procedures of claim 11 wherein said electrically insulative coating is ceramic.

15. The bipolar electrosurgical instrument for biopsy procedures of claim 11 wherein said electrically insulative coating has a thickness in the range of 1–5 mils.

16. A bipolar electrosurgical instrument for biopsy procedures comprising:
    (a) an elongated tubular member having a proximal end, a distal end, and a lumen extending therebetween;
    (b) first and second biopsy jaw members, each comprising a coated tissue collecting receptacle including a cutting edge, an intermediate insulating coating on an exterior of said receptacle, and a conductive coating on an interior of said intermediate coating;
    (c) means pivotally joining first and second biopsy jaw members to the distal end of said elongated tubular member with their respective cutting edges facing one another;
    (d) a handle affixed to the proximal end of said tubular member;
    (e) means coupled with said handle and extending through said lumen for imparting a closing and opening movement to at least one of said first and second biopsy jaw members relative to the other;
    (f) a spacing means for electrically isolating said first biopsy jaw member from said second biopsy member; and
    (g) means extending through said lumen for applying a voltage between said conductive coatings.

17. The bipolar electrosurgical instrument for biopsy procedures of claim 16 wherein said conductive coating includes metal traces.

18. The bipolar electrosurgical instrument for biopsy procedures of claim 16 wherein said conductive coating has a thickness in the range of 1–5 mils.

19. The bipolar biopsy instrument for biopsy procedures of claim 16 wherein said insulating coating is a ceramic.

20. The bipolar electrosurgical instrument for biopsy procedures of claim 16 wherein said insulating coating has a thickness in the range of 1–5 mils.

* * * * *